(12) United States Patent
Kurasawa

(10) Patent No.: US 11,204,314 B2
(45) Date of Patent: Dec. 21, 2021

(54) CALIBRATION APPARATUS AND CALIBRATION CURVE CREATION METHOD

(71) Applicant: Seiko Epson Corporation, Tokyo (JP)

(72) Inventor: Hikaru Kurasawa, Shiojiri (JP)

(73) Assignee: Seiko Epson Corporation

( * ) Notice: Subject to any disclaimer, the term of this patent is extended or adjusted under 35 U.S.C. 154(b) by 493 days.

(21) Appl. No.: 15/708,598

(22) Filed: Sep. 19, 2017

(65) Prior Publication Data

US 2018/0088033 A1 Mar. 29, 2018

(30) Foreign Application Priority Data

Sep. 26, 2016 (JP) .............................. JP2016-186723

(51) Int. Cl.
  G01N 21/27 (2006.01)
  G01N 21/35 (2014.01)
  (Continued)

(52) U.S. Cl.
  CPC ........... G01N 21/274 (2013.01); G01N 21/35 (2013.01); A61B 5/1455 (2013.01); G01J 3/28 (2013.01);
  (Continued)

(58) Field of Classification Search
  None
  See application file for complete search history.

(56) References Cited

U.S. PATENT DOCUMENTS

| | | | | |
|---|---|---|---|---|
| 7,438,855 | B2 * | 10/2008 | Sota | .................... A61B 5/14532 422/547 |
| 9,921,201 | B2 * | 3/2018 | Arai | .................... G01N 33/0098 |

(Continued)

FOREIGN PATENT DOCUMENTS

| | | | |
|---|---|---|---|
| EP | 2784484 | A1 * | 10/2014 |
| JP | 2006-271815 | A | 10/2006 |
| JP | 2013-036973 | A | 2/2013 |
| JP | 2013-160574 | A | 8/2013 |
| JP | 2013160575 | A * | 8/2013 |

(Continued)

OTHER PUBLICATIONS

Machine Translation for JP2016075588 (Year: 2016).*

(Continued)

*Primary Examiner* — Catherine T. Rastovski
*Assistant Examiner* — Leonard S Liang
(74) *Attorney, Agent, or Firm* — Harness, Dickey & Pierce, P.L.C.

(57) ABSTRACT

A calibration data acquisition unit (a) acquires Q optical spectra, S evaluation spectra, and a reference spectrum of a target component, (b) extracts R subsets from a set of the optical spectra, (c) performs independent component analysis in which component amounts are treated as independent components on each subset so as to acquire component natural spectra and component calibration spectra, (d) obtains an inner product value between the component calibration spectrum and the evaluation spectrum, (e) obtains a correlation degree between a component amount for the target component and the inner product value with respect to each component calibration spectrum, (f) obtains a similarity between each component natural spectrum and a reference spectrum, (g) selects a component calibration spectrum causing a comprehensive evaluation value based on the correlation degree and the similarity to be greatest as the target component calibration spectrum, and (h) creates a calibration curve.

3 Claims, 11 Drawing Sheets

(51) Int. Cl.
*G01N 21/359* (2014.01)
*A61B 5/1455* (2006.01)
*H01J 49/00* (2006.01)
*G01J 3/28* (2006.01)

(52) U.S. Cl.
CPC ..... *G01N 21/359* (2013.01); *G01N 2201/127* (2013.01); *H01J 49/0036* (2013.01)

(56) References Cited

U.S. PATENT DOCUMENTS

| | | | |
|---|---|---|---|
| 2004/0207625 A1* | 10/2004 | Griffin | A61B 5/0059 345/440 |
| 2006/0013454 A1* | 1/2006 | Flewelling | A61B 1/042 382/128 |
| 2012/0065948 A1* | 3/2012 | Tan | G01N 21/359 703/2 |
| 2013/0197816 A1* | 8/2013 | Kurasawa | G01N 21/274 702/27 |
| 2014/0297197 A1* | 10/2014 | Kurasawa | G01N 33/0098 702/19 |
| 2015/0025340 A1* | 1/2015 | Kanai | A61B 5/1455 600/316 |
| 2015/0025851 A1* | 1/2015 | Arai | G01N 33/0098 702/189 |
| 2016/0054343 A1* | 2/2016 | Holmes | G01N 35/026 506/2 |
| 2016/0091417 A1* | 3/2016 | Kurasawa | G01N 21/359 702/87 |
| 2016/0097676 A1* | 4/2016 | Kurasawa | A61B 5/01 702/104 |
| 2016/0097712 A1* | 4/2016 | Shimizu | G01N 21/274 702/19 |
| 2016/0103018 A1* | 4/2016 | Kurasawa | G01J 3/0297 702/104 |
| 2016/0103063 A1* | 4/2016 | Kurasawa | G01N 21/359 250/252.1 |
| 2016/0370396 A1* | 12/2016 | Wasson | G01N 35/026 |
| 2017/0045356 A1 | 2/2017 | Pandev et al. | |
| 2018/0088032 A1* | 3/2018 | Kurasawa | G01N 21/274 |
| 2018/0088034 A1* | 3/2018 | Eguchi | G01N 21/274 |
| 2018/0088035 A1* | 3/2018 | Kurasawa | G01N 21/274 |

FOREIGN PATENT DOCUMENTS

| | | | | |
|---|---|---|---|---|
| JP | 2013160576 A | * | 8/2013 | |
| JP | 2016-065803 A | | 4/2016 | |
| JP | 2016075588 A | * | 5/2016 | |
| WO | WO-9207275 A1 | * | 4/1992 | G01N 21/274 |

OTHER PUBLICATIONS

Keiji Uetsuki et al., "Prediction of Facial Color Variation by Using Independent Component Analysis and Evaluation on Facial Images", 2001, Journal of the Society of Photographic Science and Technology of Japan, 4th Issue of vol. 64, pp. 255-263, with English translation.

* cited by examiner

CALIBRATION APPARATUS AND CALIBRATION CURVE CREATION METHOD

BACKGROUND

1. Technical Field

The present invention relates to a calibration technique of obtaining a component amount of a target component from measured data of a subject, and an independent component analysis technique of determining an independent component on the basis of measured data such as an optical spectrum.

2. Related Art

In the related art, there is a calibration method of obtaining a component amount of a target component by using independent component analysis (ICA). The independent component analysis of the related art is a method of estimating signal sources as independent components on the premise that the signal sources (for example, an optical spectra) derived from a plurality of components are independent components. For example, JP-A-2013-36973 discloses a calibration technique in which an optical spectrum is acquired by performing spectrometry on a green vegetable, a spectrum derived from chlorophyll is estimated as an independent component by performing independent component analysis on the optical spectrum, and a chlorophyll amount in a new green vegetable sample is determined by using the estimated spectrum.

Meanwhile, in order to sufficiently accurately perform independent component analysis, the condition that a plurality of independent components to be estimated are statistically independent from each other is required to be established. However, in a certain kind of measured data, such a condition for performing accurate independent component analysis may not be established.

In this case, there is a probability that optical spectra cannot be accurately estimated even if normal independent component analysis in which optical spectra derived from a plurality of components are treated as independent components is performed. Therefore, a technique of performing independent component analysis with high accuracy or a technique of calibrating a target component with high accuracy is desirable even in a case where the condition that optical spectra derived from a plurality of components are "statistically independent from each other" is not satisfied. This problem is not limited to calibration of a target component using an optical spectrum including a near-infrared region, and is common to other techniques of performing independent component analysis on other measured data or measured signals.

SUMMARY

An advantage of some aspects of the invention is to solve at least a part of the problems described above, and the invention can be implemented as the following forms or application examples.

(1) According to a first aspect of the invention, a calibration apparatus obtaining a component amount for a target component in a test object is provided. The calibration apparatus includes an optical spectrum acquisition unit that acquires an optical spectrum obtained through spectrometry on the test object; a calibration data acquisition unit that acquires calibration data including a target component calibration spectrum corresponding to the target component, and a single regression formula indicating a calibration curve; an inner product value calculation unit that computes an inner product value between the optical spectrum acquired for the test object and the target component calibration spectrum; and a component amount calculation unit that calculates a component amount for the target component corresponding to an inner product value obtained by the inner product value calculation unit by using the single regression formula indicating a relationship between the inner product value and a component amount for the target component. The calibration data acquisition unit performs (a) a process of acquiring Q optical spectra obtained through spectrometry on Q (where Q is an integer of 3 or more) first samples each containing N (where N is an integer of 1 or more) components including the target component, S evaluation spectra obtained through spectrometry on S (where S is an integer of 3 or more) second samples in which a component amount for the target component is known, and a reference spectrum corresponding to the target component, (b) a process of extracting R (where R is an integer of 2 or more) subsets from a set of the Q optical spectra, (c) a process of determining a component natural spectrum matrix formed of N component natural spectra derived from the N components, and N component calibration spectra which are a row vector of a general inverse matrix of the component natural spectrum matrix by performing independent component analysis in which component amounts for the N components are treated as independent components in each sample on each of the R subsets, and acquiring a total of R×N component natural spectra and R×N component calibration spectra, (d) a process of obtaining S inner product values by performing an inner product between each of the R×N component calibration spectra and the S evaluation spectra, (e) a process of obtaining a correlation degree between a component amount for the target component in the S second samples and the S inner product values with respect to each of the R×N component calibration spectra, (f) a process of obtaining a similarity between a component natural spectrum corresponding to each component calibration spectrum and the reference spectrum with respect to each of the R×N component calibration spectra, (g) a process of obtaining a comprehensive evaluation value calculated by using the correlation degree and the similarity with respect to each of the R×N component calibration spectra, and, from among the R×N component calibration spectra, selecting a component calibration spectrum causing the comprehensive evaluation value to be greatest as the target component calibration spectrum, and (h) a process of creating, as the calibration curve, a single regression formula indicating a relationship between an inner product value obtained through an inner product between the S evaluation spectra and the target component calibration spectrum, and a component amount for the target component contained in the S second samples.

According to the calibration apparatus, since independent component analysis in which component amounts for N components in each sample are treated as independent components is performed, the independent component analysis can be performed with high accuracy, and thus calibration of a target component can be performed with high accuracy, even in a case where optical spectra derived from a plurality of components are not independent from each other. Since plurality of subsets are extracted from a set of Q optical spectra, and independent component analysis in which a component amount is treated as an independent component is performed on each of the subsets, even in a case where a component amount distribution in the whole set of the Q optical spectra is a Gaussian distribution, and thus there is a subset in which independency is deficient, independency is improved since a component amount distribution is a more non-Gaussian distribution in several subsets, and thus it is possible to obtain a target component calibration spectrum with high accuracy. As a result, it is possible to perform calibration with higher accuracy. Among the R×N component calibration spectra, a component calibration spectrum causing the comprehensive evaluation value of the correlation degree and the similarity to be greatest is selected as a target component calibration spectrum, it is possible to select a target component calibration spectrum suitable for calibration of a sample.

(2) In the process (c), the calibration data acquisition unit may (1) use an equation X=YW in which an optical spectrum matrix X having optical spectra obtained through spectrometry on each sample as column vectors is the same as a product between a component natural spectrum matrix Y having unknown component natural spectra derived from the respective components among the N components contained in each sample as column vectors and a component amount matrix W having unknown component amounts for the N components in each of the samples as column vectors, and perform independent component analysis in which the respective column vectors forming the component amount matrix W are treated as independent components, so as to determine the component amount matrix W and the component natural spectrum matrix Y, and (2) employ inverse matrix row vectors respectively corresponding to the N components in a general inverse matrix $Y^\dagger$ of the component natural spectrum matrix Y determined through the independent component analysis, as the component calibration spectra corresponding to the respective components.

According to this configuration, it is possible to determine a component calibration spectrum corresponding to each component with high accuracy.

(3) According to a second aspect of the invention, a calibration curve creation method performed by the calibration data acquisition unit in the first aspect is provided.

According to the calibration method, in the same manner as in the first aspect, it is possible to obtain target component calibration spectrum with high accuracy, and to perform calibration with high accuracy.

The invention may be realized in aspects such as an electronic apparatus including the above-described apparatus, a computer program for realizing functions of the respective units of the apparatus, and a non-transitory storage medium which stores the computer program thereon.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
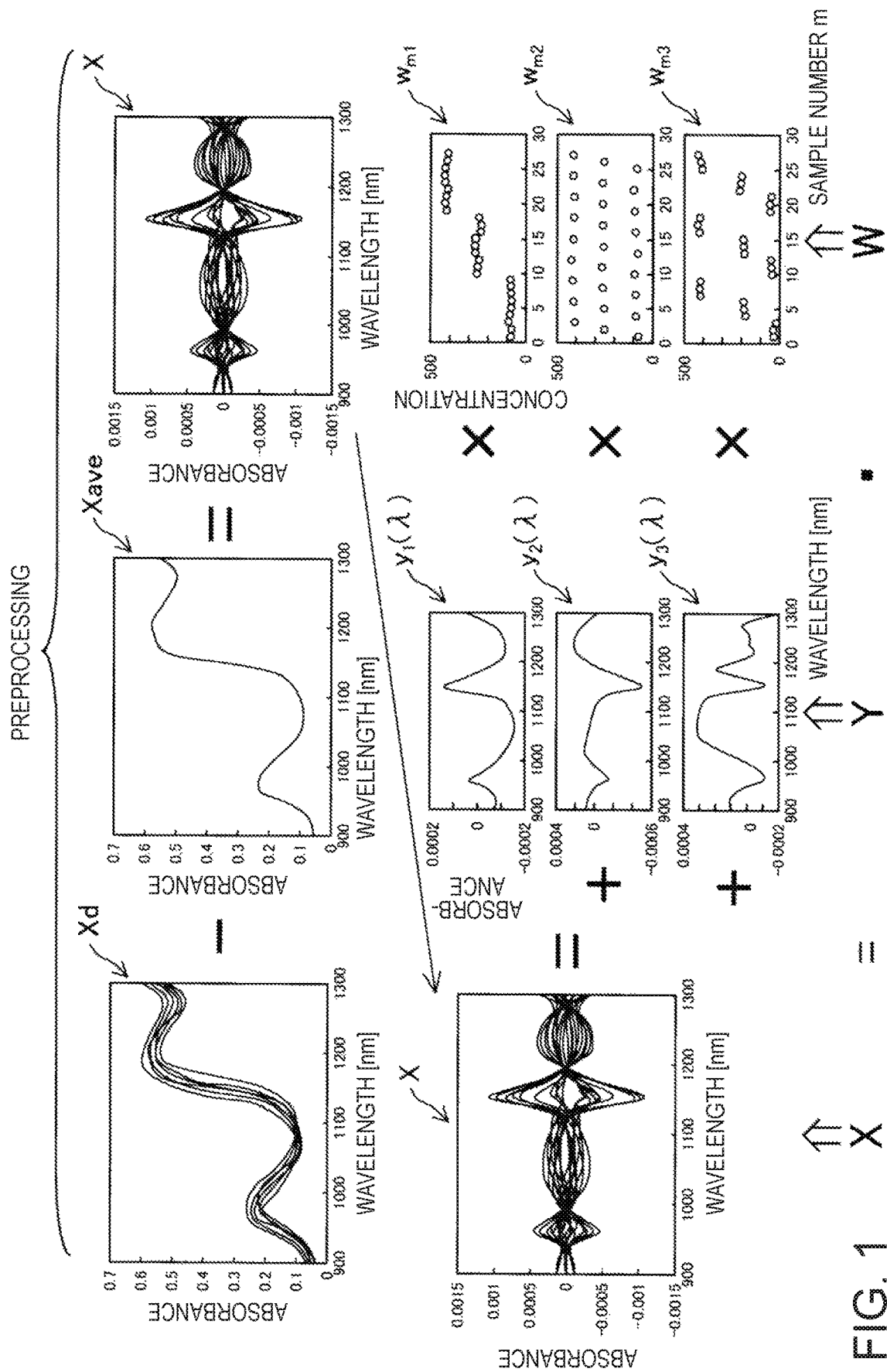
FIG. 1 is a diagram illustrating an overview of independent component analysis in which component amounts are treated as independent components.

Hereinafter, an embodiment of the invention will be described in the following order.

A. Overview of independent component analysis in which component amounts are treated as independent components
B. Overview of calibration curve creation process and calibration process
C. Configuration of calibration apparatus and process content thereof in embodiment
D. Content of calibration data acquisition process
E. Example
F. Modification examples A. OVERVIEW OF INDEPENDENT COMPONENT ANALYSIS IN WHICH COMPONENT AMOUNTS ARE TREATED AS INDEPENDENT COMPONENTS Independent component analysis used in an embodiment described below is greatly different from typical independent component analysis in which component-derived measured data (for example, an optical spectrum) is treated as an independent component in that a component amount for a component is treated as an independent component. Therefore, first, a description will be made of a difference between the typical independent component analysis and the independent component analysis in which a component amount is treated as an independent component. Hereinafter, for convenience of description, a description will be made of a case of using an optical spectrum of a test object (also referred to as a "sample") as measured data, but the independent component analysis in which a component amount is treated as an independent component is applicable to different kinds of signals or data such as a sound signal or an image.

In the typical independent component analysis, for example, optical spectra $x_1(\lambda)$, $x_2(\lambda)$, and $x_3(\lambda)$ obtained through spectrometry on a plurality of samples are expressed as in the following Equation (1) as a linear combination of component natural spectra $s_1(\lambda)$, $s_2(\lambda)$, and $s_3(\lambda)$ derived from a plurality of components contained in each sample.

$$\left. \begin{array}{l} x_1(\lambda) = a_{11}s_1(\lambda) + a_{12}s_2(\lambda) + a_{13}s_3(\lambda) \\ x_2(\lambda) = a_{21}s_1(\lambda) + a_{22}s_2(\lambda) + a_{23}s_3(\lambda) \\ x_3(\lambda) = a_{31}s_1(\lambda) + a_{32}s_2(\lambda) + a_{33}s_3(\lambda) \end{array} \right\} \quad (1)$$

Here, $a_{11}$, $a_{12}$, ..., and $a_{33}$ are weighting factors indicating component amounts for the respective components. Herein, for convenience of description, the number of samples and the number of components in optical spectra are assumed to be all three.

The above Equation (1) is expressed as in the following Equation (2) in terms of a matrix.

$$\begin{bmatrix} x_1(\lambda) \\ x_2(\lambda) \\ x_3(\lambda) \end{bmatrix} = A \begin{bmatrix} s_1(\lambda) \\ s_2(\lambda) \\ s_3(\lambda) \end{bmatrix} \quad (2)$$

$$A = \begin{bmatrix} a_{11} & a_{12} & a_{13} \\ a_{21} & a_{22} & a_{23} \\ a_{31} & a_{32} & a_{33} \end{bmatrix}$$

In the typical independent component analysis, unknown component natural spectra $s_1(\lambda)$, $s_2(\lambda)$, and $s_3(\lambda)$ derived from a plurality of components are treated as components which are independent from each other, and are subjected to independent component analysis by using the above Equation (2). In this case, in order to sufficiently accurately perform independent component analysis, the condition that a plurality of component natural spectra $s_1(\lambda)$, $s_2(\lambda)$, and $s_3(\lambda)$ are statistically independent from each other is required to be established.

However, the condition for performing accurate independent component analysis may not be established depending on property of measured data. In this case, optical spectra derived from a plurality of components may not satisfy the condition of being "statistically independent from each other". In this case, even if the typical independent component analysis is performed by using the above Equation (2), the component natural spectra $s_1(\lambda)$, $s_2(\lambda)$, and $s_3(\lambda)$ or the component amount matrix A cannot be accurately estimated.

The present inventor of the invention has found that the component natural spectra $s_1(\lambda)$, $s_2(\lambda)$, and $s_3(\lambda)$ or the component amount matrix A can be accurately estimated or determined by employing the independent component analysis in which a component amount is treated as an independent component instead of the above-described typical independent component analysis.

In the independent component analysis in which a component amount is treated as an independent component, the following equation is used instead of the above Equation (2).

$$[x_1(\lambda)^T \; x_2(\lambda)^T \; x_3(\lambda)^T] = [s_1(\lambda)^T \; s_2(\lambda)^T \; s_3(\lambda)^T] A^T \quad (3)$$

$$A^T = \begin{bmatrix} a_{11} & a_{21} & a_{31} \\ a_{12} & a_{22} & a_{32} \\ a_{13} & a_{23} & a_{33} \end{bmatrix}$$

Here, the superscript "T" added to the matrix symbol indicates a transposed matrix. Equation (3) is obtained by transposing both of the sides in the above Equation (2).

In the independent component analysis in which a component amount is treated as an independent component, in the above Equation (3), the column vectors $[a_{11} \; a_{12} \; a_{13}]^T$, $[a_{21} \; a_{22} \; a_{23}]^T$, and $[a_{31} \; a_{32} \; a_{33}]^T$ of the component amount matrix $A^T$ are respectively treated as independent components, and independent component analysis is performed. These column vectors indicate component amounts for a plurality of components in each sample.

The independent component analysis in which a component amount is treated as an independent component is an analysis method employed through the following examination. As described above, there is a case where component natural spectra derived from a plurality of components do not satisfy the condition of being statistically independent from each other. However, although component natural spectra derived from a plurality of components are not statistically independent from each other, if the condition that component amounts (for example, concentrations) for the plurality of components have no relation to each other and are statistically independent from each other is established, in a case where component amounts (that is, the respective column vectors forming the component amount matrix $A^T$ in the above Equation (3)) for a plurality of components in each sample are treated as independent components, and independent component analysis is performed, it is possible to accurately estimate or determine the component amount matrix $A^T$, and also to accurately estimate or determine the component natural spectra $s_1(\lambda)$, $s_2(\lambda)$, and $s_3(\lambda)$.

If the above Equation (3) is generalized, the following Equation (4) is obtained.

$$X^T = S^T A^T \quad (4)$$

$$X^T = \begin{bmatrix} x_1(\lambda_1) & \cdots & x_M(\lambda_1) \\ \vdots & \ddots & \vdots \\ x_1(\lambda_K) & \cdots & x_M(\lambda_K) \end{bmatrix}$$

$$S^T = \begin{bmatrix} s_1(\lambda_1) & \cdots & s_N(\lambda_1) \\ \vdots & \ddots & \vdots \\ s_1(\lambda_K) & \cdots & s_N(\lambda_K) \end{bmatrix}$$

$$A^T = \begin{bmatrix} a_{11} & \cdots & a_{M1} \\ \vdots & \ddots & \vdots \\ a_{1N} & \cdots & a_{MN} \end{bmatrix}$$

Here, K indicates the number of measurement points of the wavelength $\lambda$ in a spectrum, M indicates the number of samples, and N indicates the number of components. A component amount $a_{mn}$ (where m is 1 to M, and n is 1 to N) is a component amount (for example, a concentration) for an n-th component in an m-th sample.

Since it is inconvenient to use matrices $X^T$, $S^T$, and $A^T$ as in the above Equation (4) with the transposition symbol, $X=X^T$, $Y=S^T$, $y_n(\lambda_k)=s_n(\lambda_k)$, $W=A^T$, and $w_{mn}=a_{mn}$ are set, and the above Equation (4) is rewritten into the following Equation (5) which is used in independent component analysis in which a component amount is treated as an independent component.

Equations used in independent component analysis in which component amount is treated as independent component:

$$X = YW \quad (5)$$

$$X = \begin{bmatrix} x_1(\lambda_1) & \cdots & x_M(\lambda_1) \\ \vdots & \ddots & \vdots \\ x_1(\lambda_K) & \cdots & x_M(\lambda_K) \end{bmatrix}$$

$$Y = \begin{bmatrix} y_1(\lambda_1) & \cdots & y_N(\lambda_1) \\ \vdots & \ddots & \vdots \\ y_1(\lambda_K) & \cdots & y_N(\lambda_K) \end{bmatrix}$$

$$W = \begin{bmatrix} w_{11} & \cdots & w_{M1} \\ \vdots & \ddots & \vdots \\ w_{1N} & \cdots & w_{MN} \end{bmatrix}$$

Here, $x_m(\lambda_k)$ indicates an spectral intensity at a wavelength $\lambda_k$ in an m-th sample, $y_n(\lambda_k)$ indicates an spectral intensity at the wavelength $\lambda_k$ derived from an n-th component, and $w_{mn}$ indicates a component amount for the n-th component in the m-th sample. K indicates the number of measurement points of the wavelength λ in a spectrum, M indicates the number of samples, and N indicates the number of components. K and M are all integers of 2 or more. N is an integer of 1 or more, and may be an integer of 2 or more.

The above Equation (5) corresponds to an equation in which an optical spectrum matrix X having optical spectra obtained through spectrometry on each sample as column vectors $[x_m(\lambda_1) \ldots x_m(\lambda_K)]^T$ is the same as a product between a component natural spectrum matrix Y having unknown component natural spectra derived from a plurality of respective components as column vectors $[y_n(\lambda_1) \ldots y_n(\lambda_K)]^T$ and a component amount matrix W having unknown component amounts indicating component amounts for a plurality of components in each sample as column vectors $[w_{m1} \ldots w_{mN}]^T$.

FIG. 1 is a diagram illustrating an overview of independent component analysis in which a component amount is treated as an independent component. FIG. 1 illustrates an example of a case where an aqueous solution containing glucose or albumin is used as a sample, and optical spectra obtained through spectrometry on a plurality of samples are used as independent component analysis objects. A measured spectrum Xd is an absorbance spectrum obtained through spectrometry. A plurality of actual measured spectra Xd show considerably approximate curves, but, in FIG. 1, for convenience of illustration, differences among the plurality of measured spectra Xd are illustrated to be exaggerated. The measured spectra Xd for a plurality of samples have values approximate to each other, and, thus, if these values are used as they are, there is a probability that the accuracy of a result obtained through independent component analysis may not be sufficiently high. For example, the influence of a solvent on a measured spectrum may change depending on the concentration of a solute (contained component), and thus the accuracy of independent component analysis may deteriorate. Therefore, as preprocessing, a subtraction calculation is performed so that an average spectrum Xave of a plurality of measured spectra Xd is subtracted from each measured spectrum Xd, and thus a difference spectrum X is obtained. In the above-described way, even in a case where the influence of a solvent on a measured spectrum changes depending on the concentration of a solute (contained component), the influence can be removed through the preprocessing, and thus it is possible to increase the accuracy of independent component analysis. The difference spectrum X is used as the optical spectrum X in the above Equation (5). If independent component analysis is performed on the difference spectrum X, the accuracy of the independent component analysis can be improved. However, preprocessing may be omitted.

The lower part in FIG. 1 illustrates a state in which the optical spectrum X is expressed by a product between the unknown component natural spectrum $y_n(\lambda)$ and the unknown component amount $w_{mn}$ according to the above Equation (5).

In the independent component analysis, the component amount matrix W is determined by treating each column vector $[w_{m1} \ldots w_{mN}]^T$ of the component amount matrix W in the above Equation (5) as an independent component and performing the independent component analysis, and, as a result, the component natural spectrum matrix Y is also determined. An independent component analysis method may employ the typical independent component analysis. For example, an independent component analysis method disclosed in JP-A-2013-160574 or JP-A-2016-65803 filed by the applicant of the present application may be used, or other independent component analysis methods may be used.

If the component natural spectrum matrix Y in the above Equation (5) is determined, a component amount w* for a plurality of components in a new sample may be obtained by integrating an optical spectrum x* obtained through spectrometry on the new sample with a general inverse matrix $Y^\dagger$ of the component natural spectrum matrix Y obtained through the independent component analysis. Specifically, the component amount w* for the components of the new sample may be obtained by using the following Equation (6).

$$w^* = Y^\dagger x^* \qquad (6)$$

$$w^* = \begin{bmatrix} w_1^* \\ \vdots \\ w_N^* \end{bmatrix}$$

$$Y^\dagger = \begin{bmatrix} y_1^\ddagger(\lambda_1) & \cdots & y_1^\ddagger(\lambda_K) \\ \vdots & \ddots & \vdots \\ y_N^\ddagger(\lambda_1) & \cdots & y_N^\ddagger(\lambda_K) \end{bmatrix}$$

$$x^* = \begin{bmatrix} x^*(\lambda_1) \\ \vdots \\ x^*(\lambda_K) \end{bmatrix}$$

Here, $w^* = [w_1^* \ldots w_N^*]^T$ is a component amount for N components included in a new sample, $Y^\dagger$ is a general inverse matrix of the component natural spectrum matrix Y obtained through independent component analysis, $y_n(\lambda_k)^\ddagger$ is a k-th element of a row vector of an n-th row in the general inverse matrix $Y^\dagger$, and $x^* = [x^*(\lambda_1) \ldots x^*(\lambda_K)]^T$ is an optical spectrum obtained through spectrometry on the new sample. The above Equation (6) may be derived by multiplying the lefts of both sides in the above Equation (5) by the general inverse matrix $Y^\dagger$ of the component natural spectrum matrix Y.

A value of a component amount $w_n^*$ for any n-th component of the new sample is obtained according to the following Equation (7) derived from the above Equation (6).

$$w_n^* = y_n^\ddagger x^* \qquad (7)$$

$$y_n^\ddagger = [y_n^\ddagger(\lambda_1) \ldots y_n^{\ddagger*}(\lambda_K)]$$

Here, $y_n^\ddagger$ is a row vector of an n-th row in the general inverse matrix $Y^\dagger$ of the component natural spectrum matrix Y. The row vector $y_n^\ddagger$ is also referred to as an "inverse matrix row vector $y_n^\ddagger$" or a "component calibration spectrum $y_n^\ddagger$". The general inverse matrix $Y^\dagger$ of the component natural spectrum matrix Y is referred to as a "component calibration spectrum matrix $Y^{\dagger}$". As mentioned above, the general inverse matrix $Y^\dagger$ may be obtained on the basis of the component natural spectrum matrix Y obtained through independent component analysis, and the component amount $w_n^*$ for the n-th component may be obtained by taking an inner product between the inverse matrix row vector $y_n^{\ddagger}$ (that is, the n-th component calibration spectrum $y_n^{\ddagger}$) corresponding to the n-th component in the general inverse matrix $Y^{\dagger}$ and the optical spectrum $x^*$ for the new sample. However, the component natural spectrum matrix Y obtained through independent component analysis is meaningless in a value of an element thereof, and has property in which a waveform thereof is proportional to a true component natural spectrum. Therefore, the component amount $w_n^*$ obtained through the inner product in the above Equation (7) is a value which is proportional to an actual component amount. An actual component amount may be obtained by applying the inner product value $w_n^*$ obtained through the inner product in the above Equation (7) to a calibration curve (described later).

As mentioned above, according to the independent component analysis in which a component amount is treated as an independent component, even in a case where component natural spectra derived from a plurality of components are not statistically independent from each other, the component amount matrix W and the component natural spectrum matrix Y (and the component calibration spectrum matrix $Y^{\dagger}$ which is a general inverse matrix) can be accurately estimated or determined.

B. OVERVIEW OF CALIBRATION CURVE CREATION PROCESS AND CALIBRATION PROCESS

Figure 2:
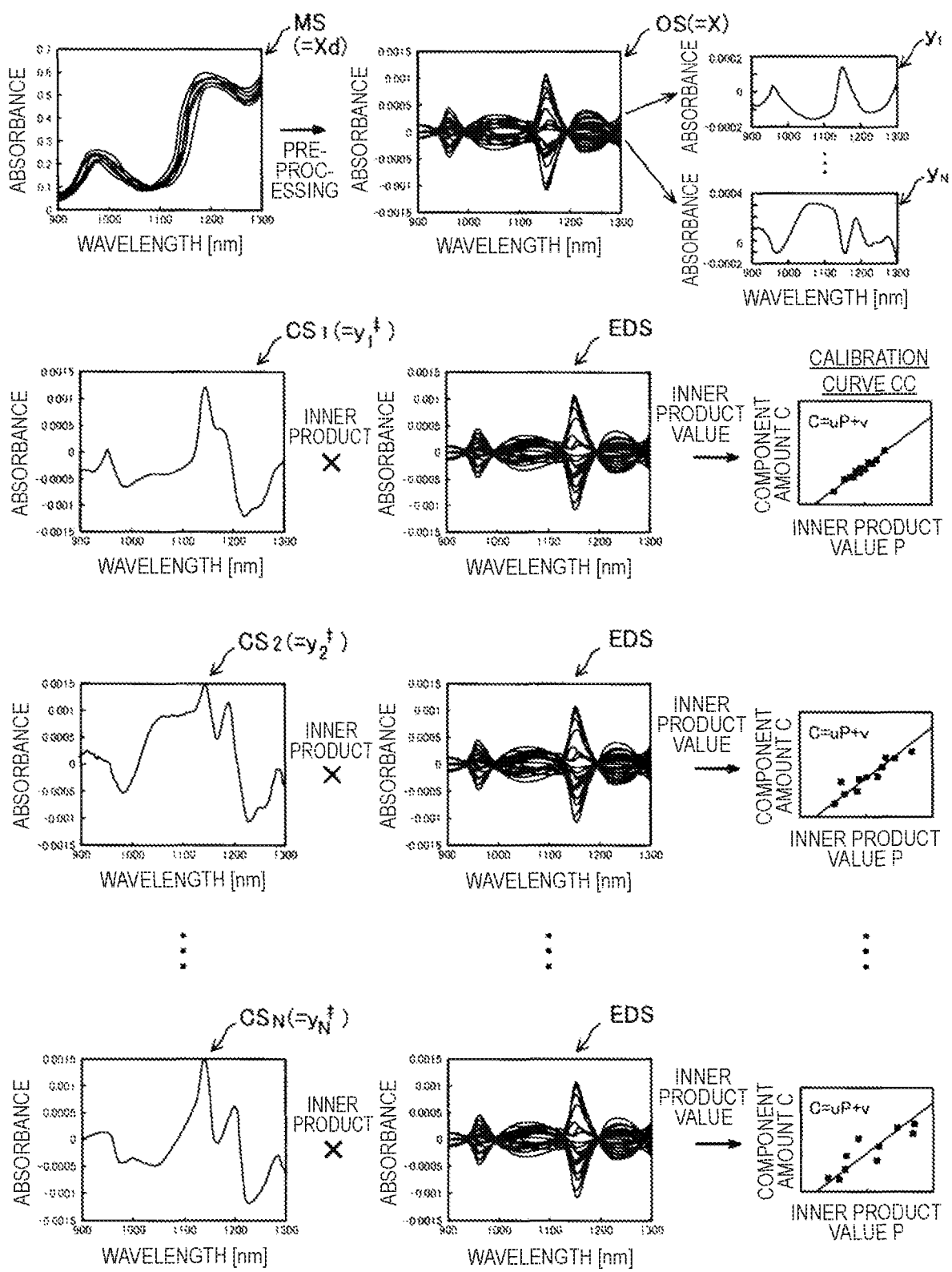
FIG. 2 is a diagram illustrating an overview of a calibration curve creation process using independent component analysis.

FIG. 2 is a diagram illustrating an overview of a calibration curve creation process using independent component analysis (ICA) in which a component amount is treated as an independent component. An upper left part in FIG. 2 illustrates examples of measured spectra MS obtained through spectrometry on a plurality of samples. The measured spectra MS corresponds to the measured spectra Xd in FIG. 1, and may be obtained through spectrometry on a sample containing a plurality of components (for example, glucose and albumin). In a typical calibration curve creation process, as a plurality of samples, known samples in which a component amount (for example, a concentration) for a target component (for example, glucose) is known are used. However, in an embodiment which will be described later, there is a difference from the typical calibration curve creation process in that samples (first samples) in which a component amount for a target component is unknown may be used as a plurality of samples for acquiring optical spectra as independent component analysis objects.

In creation of a calibration curve, first, preprocessing is performed on the measured spectra MS, and thus optical spectra OS (the optical spectra X having undergone preprocessing in FIG. 1) having undergone the preprocessing are created. As the preprocessing, for example, preprocessing including normalization of the measured spectra MS is performed. In the preprocessing, a subtraction calculation described in FIG. 1 is also preferably performed in addition to normalization. In the preprocessing, project on null space (PNS) may be performed in order to remove a baseline variation in the measured spectra MS. However, in a case where initial measured spectra MS have characteristics of not requiring preprocessing (for example, in a case where the measured spectra MS do not vary due to normalization), preprocessing may be omitted, and the measured spectra MS may be used as the optical spectra OS without being changed.

Next, independent component analysis in which a component amount is treated as an independent component is performed on a plurality of optical spectra OS, and thus a plurality of component calibration spectra $CS_1$ to $CS_N$ are obtained. The number in the parenthesis indicates a component number. The plurality of component calibration spectra $CS_1$ to $CS_N$ correspond to the above-described component calibration spectra $y_n^{\ddagger}$.

A lower part in FIG. 2 illustrates a method of creating a calibration curve by using the plurality of component calibration spectra $CS_1$ to $CS_N$ obtained in the above-described way. Herein, first, optical spectra EDS regarding a plurality of known samples (second samples) in which a component amount for a target component is known are acquired. The optical spectra EDS are obtained by performing, as necessary, the above-described preprocessing on measured spectra which are obtained through spectrometry on the known samples. The optical spectra EDS are referred to as "evaluation spectra EDS". Next, an inner product value between the individual evaluation spectra EDS and the component calibration spectrum $CS_n$ is computed. The computation of the inner product value is a calculation in which each of the evaluation spectra EDS and the component calibration spectrum $CS_n$ are treated as a single vector, and an inner product between the two vectors is taken, and, as a result, a single inner product value is obtained. Therefore, if inner products between the same component calibration spectrum $CS_n$ and a plurality of evaluation spectra EDS are computed, a plurality of inner product values corresponding to a plurality of known samples are obtained with respect to the same component calibration spectrum $CS_n$. A lower right part in FIG. 2 shows diagrams in which inner product values P regarding a plurality of known samples are taken on a transverse axis, a known component amount C for a target component contained in the plurality of known samples is taken on a longitudinal axis, and the values are plotted. If the n-th component calibration spectrum $CS_n$ used for an inner product is a spectrum corresponding to a target component, as in the example illustrated in FIG. 2, the inner product value P and the component amount C for the target component of each known sample have a strong correlation. Therefore, from among the plurality of component calibration spectra $CS_1$ to $CS_N$ obtained through the independent component analysis, the component calibration spectrum $CS_n$ having the strongest correlation (the greatest correlation degree) may be selected as a target component calibration spectrum corresponding to the target component. As an evaluation value for such selection, evaluation values other than the correlation degree may be used. In the example illustrated in FIG. 2, the first component calibration spectrum $CS_1$ is a target component calibration spectrum corresponding to the target component (for example, glucose). A calibration curve CC is represented as a straight line given by a single regression formula C=uP+v for plotting the inner product value P and the component amount C.

Figure 3:
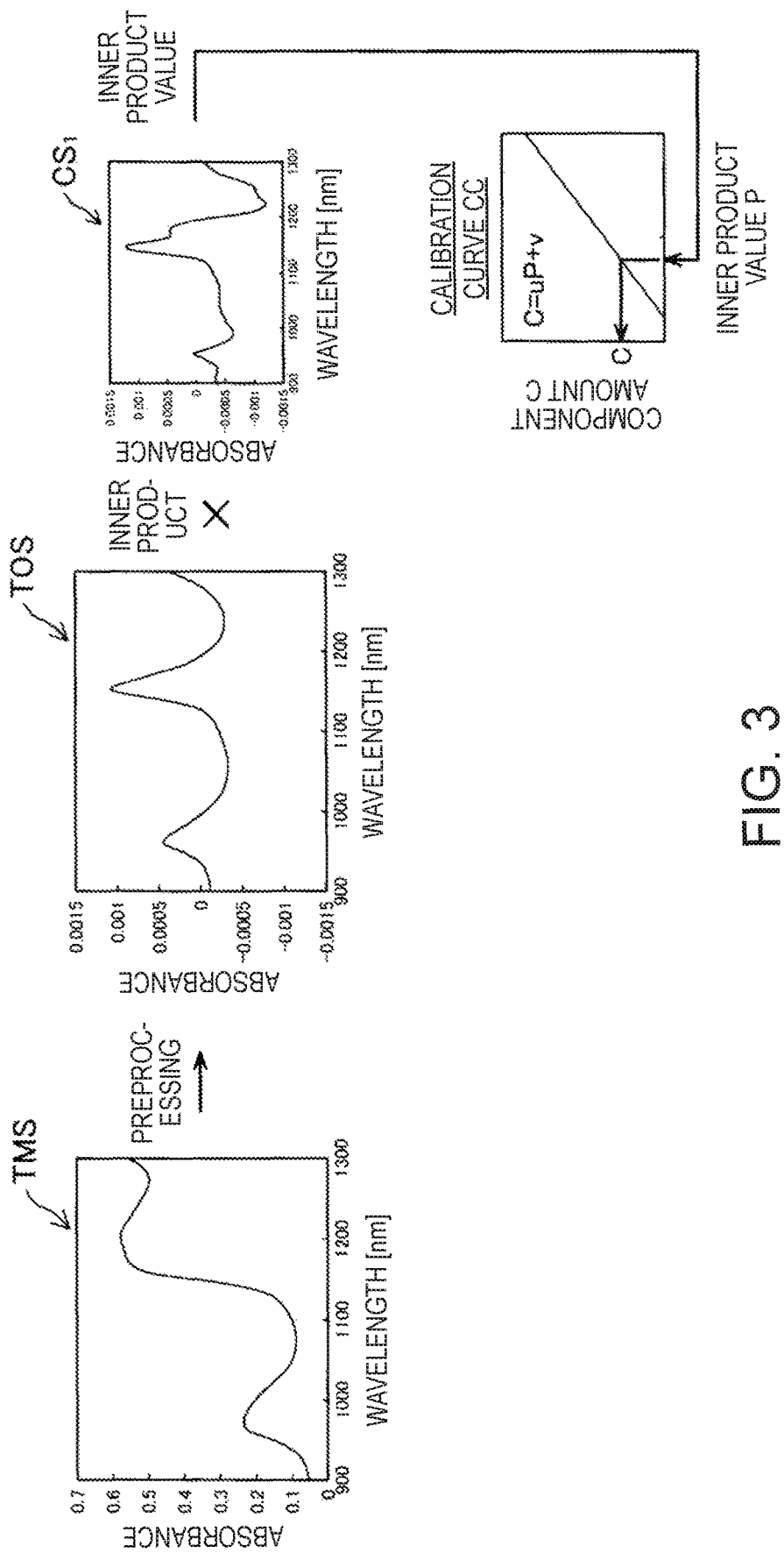
FIG. 3 is a diagram illustrating an overview of a target component calibration process.

FIG. 3 is a diagram illustrating an overview of a target component calibration process using a calibration curve. The calibration process is performed by using the target component calibration spectrum $CS_1$ and the calibration curve CC obtained through the calibration curve creation process illustrated in FIG. 2. In the calibration process, first, a measure spectrum TOS of a test object in which a component amount for a target component is unknown is acquired. Next, preprocessing is performed on the measure spectrum TOS as necessary, and thus an optical spectrum TOS having undergone the preprocessing is created. This preprocessing is the same processing as the preprocessing used for creation of the calibration curve. In the preprocessing during creation of the calibration curve, in a case where a subtraction calculation described in FIG. 1 is performed, the average spectrum Xave used during creation of the calibration curve may be subtracted from the measure spectrum TOS. An inner product between the optical spectrum TOS obtained in the above-described way and the target component calibration spectrum $CS_1$ is taken, and thus an inner product value P regarding the optical spectrum TOS is calculated. If the inner product value P is applied to the calibration curve CC, a component amount C for the target component contained in the test object can be determined.

C. CONFIGURATION OF CALIBRATION APPARATUS AND PROCESS CONTENT THEREOF IN EMBODIMENT

Figure 4:
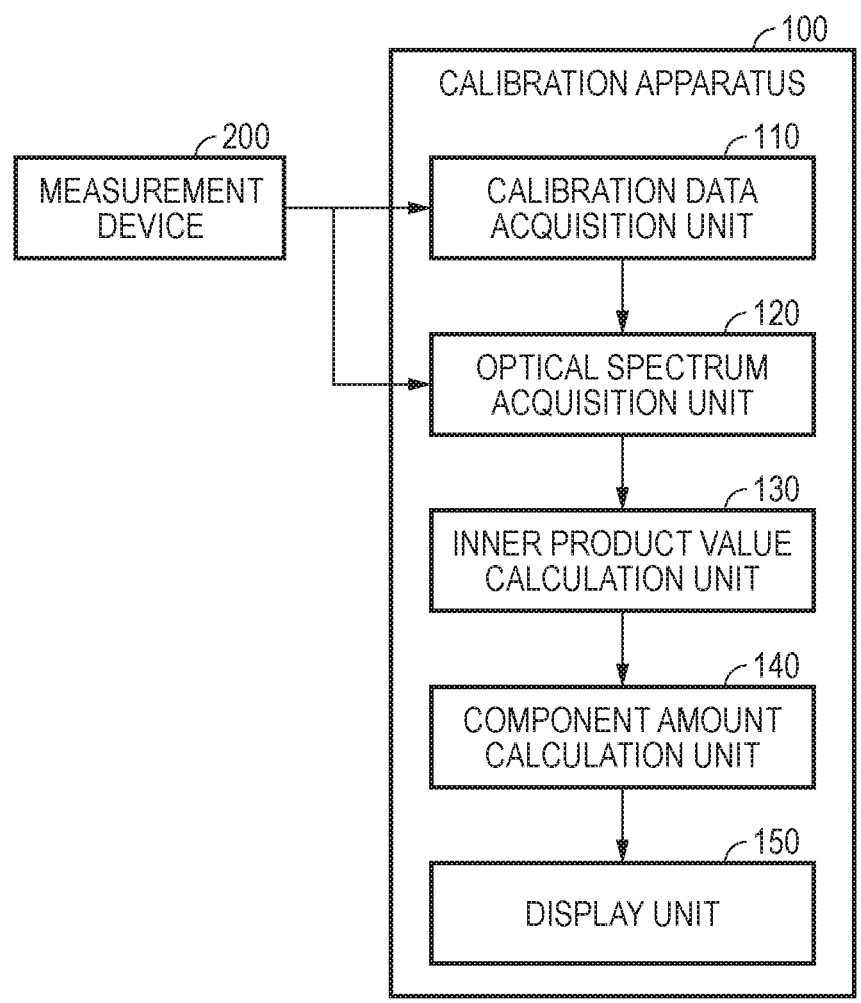
FIG. 4 is a block diagram illustrating a configuration of a calibration apparatus in an embodiment.

FIG. 4 is a block diagram illustrating a configuration of a calibration apparatus 100 in an embodiment. The calibration apparatus 100 includes a calibration data acquisition unit 110, an optical spectrum acquisition unit 120, an inner product value calculation unit 130, a component amount calculation unit 140, and a display unit 150. A measurement device 200 for acquiring measured data is connected to the calibration apparatus 100. The measurement device 200 is, for example, a spectrometer measuring spectral absorbance of a sample. The measurement device 200 is not limited to a spectrometer, and various measurement devices suitable for characteristics of target components can be used.

The calibration apparatus 100 may be implemented by, for example, an electronic apparatus for use in calibration only, and may be implemented by a general purpose computer. Functions of the respective units 110 to 150 of the calibration apparatus 100 may be implemented by any computer programs or hardware circuits.

Figure 5:
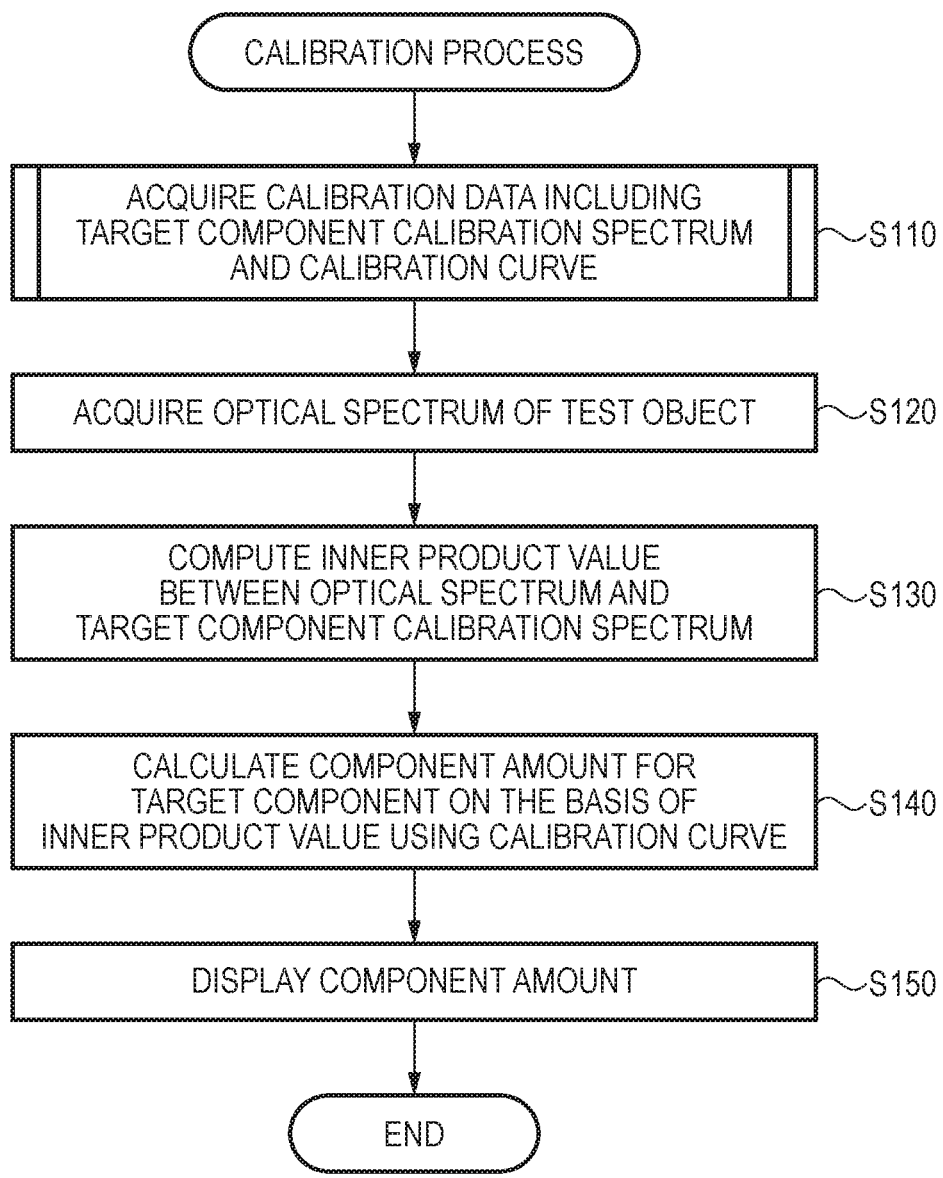
FIG. 5 is a flowchart illustrating procedures of a calibration process.

FIG. 5 is a flowchart illustrating procedures of a calibration process performed by the calibration apparatus 100. In step S110, the calibration data acquisition unit 110 (FIG. 4) acquires calibration data including a target component calibration spectrum ($CS_1$ in the example illustrated in FIG. 2) and the calibration curve CC. Details of the calibration data acquisition process in the present embodiment will be described later.

In step S120, the optical spectrum acquisition unit 120 acquires the optical spectrum TOS (FIG. 3) of a test object by using the measurement device 200. As described in FIG. 3, the optical spectrum TOS is obtained by performing preprocessing on a measure spectrum obtained through spectrometry, as necessary. Therefore, the optical spectrum acquisition unit 120 preferably has a function of performing the preprocessing. In step S130, the inner product value calculation unit 130 calculates the inner product value P (FIG. 3) between the optical spectrum TOS and the target component calibration spectrum $CS_1$. In step S140, the component amount calculation unit 140 calculates the component amount C corresponding to the inner product value P obtained in step S130 by using the calibration curve CC. The component amount C is a component amount (for example, a glucose concentration) for the target component in the test object. In step S150, the component amount C is displayed on the display unit 150. Instead of the component amount C being displayed, the component amount C may be transmitted to another electronic apparatus, and other desired processes (for example, a notification sent to a test object using an electronic mail) may be performed.

D. CONTENT OF CALIBRATION DATA ACQUISITION PROCESS

Figure 6:
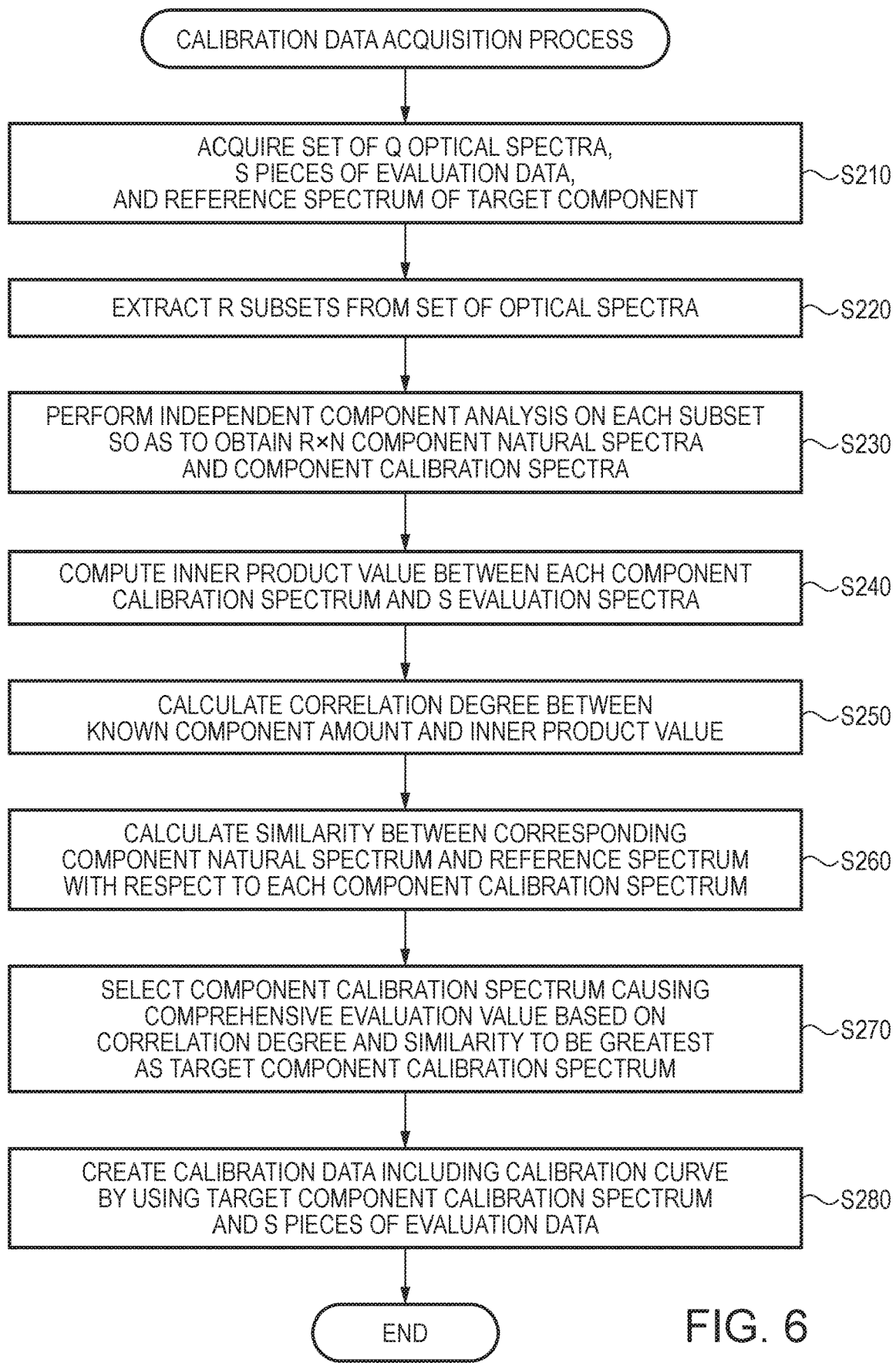
FIG. 6 is a flowchart illustrating a calibration data acquisition process.
Figure 7:
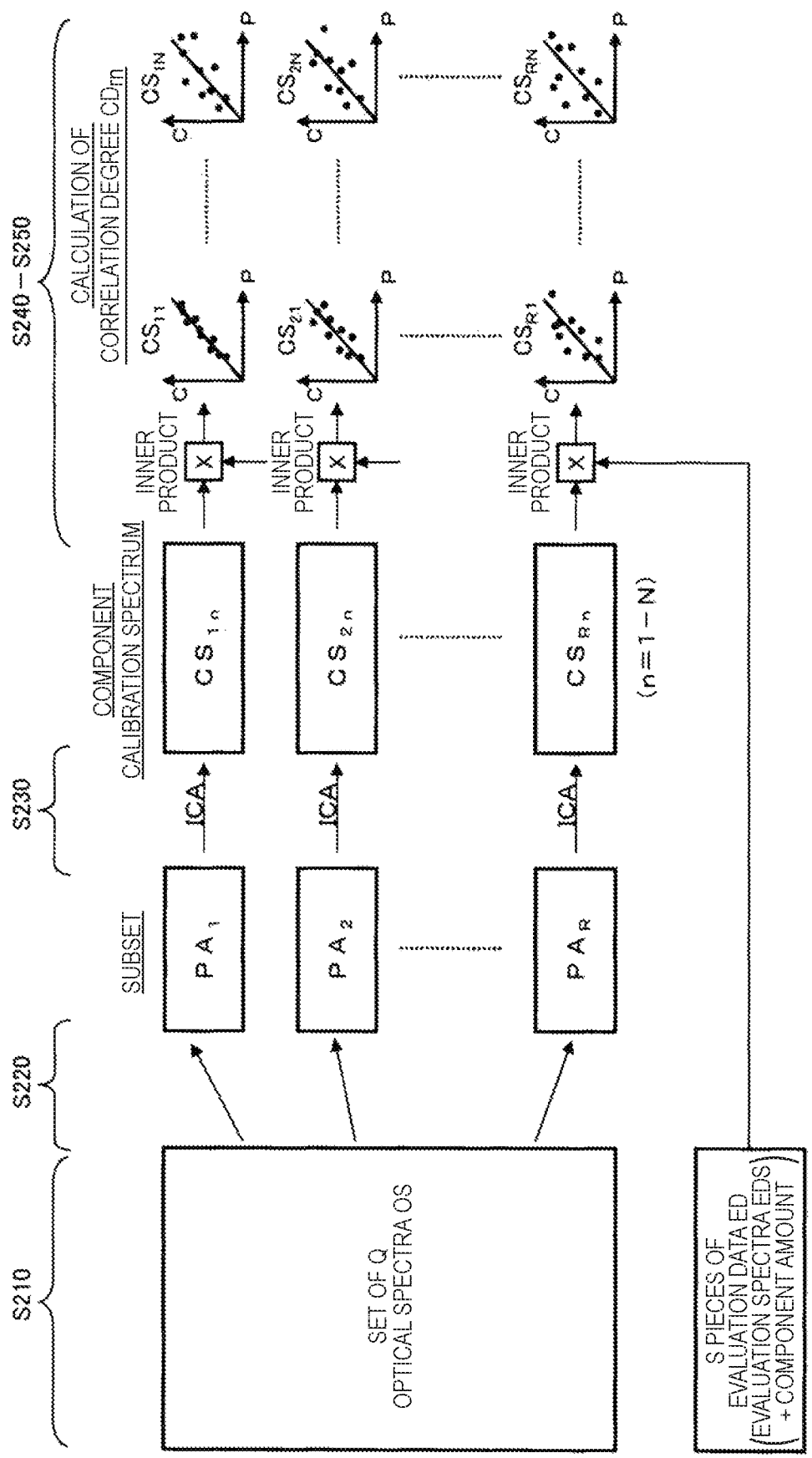
FIG. 7 is a diagram illustrating the content of the calibration data acquisition process.
Figure 8:
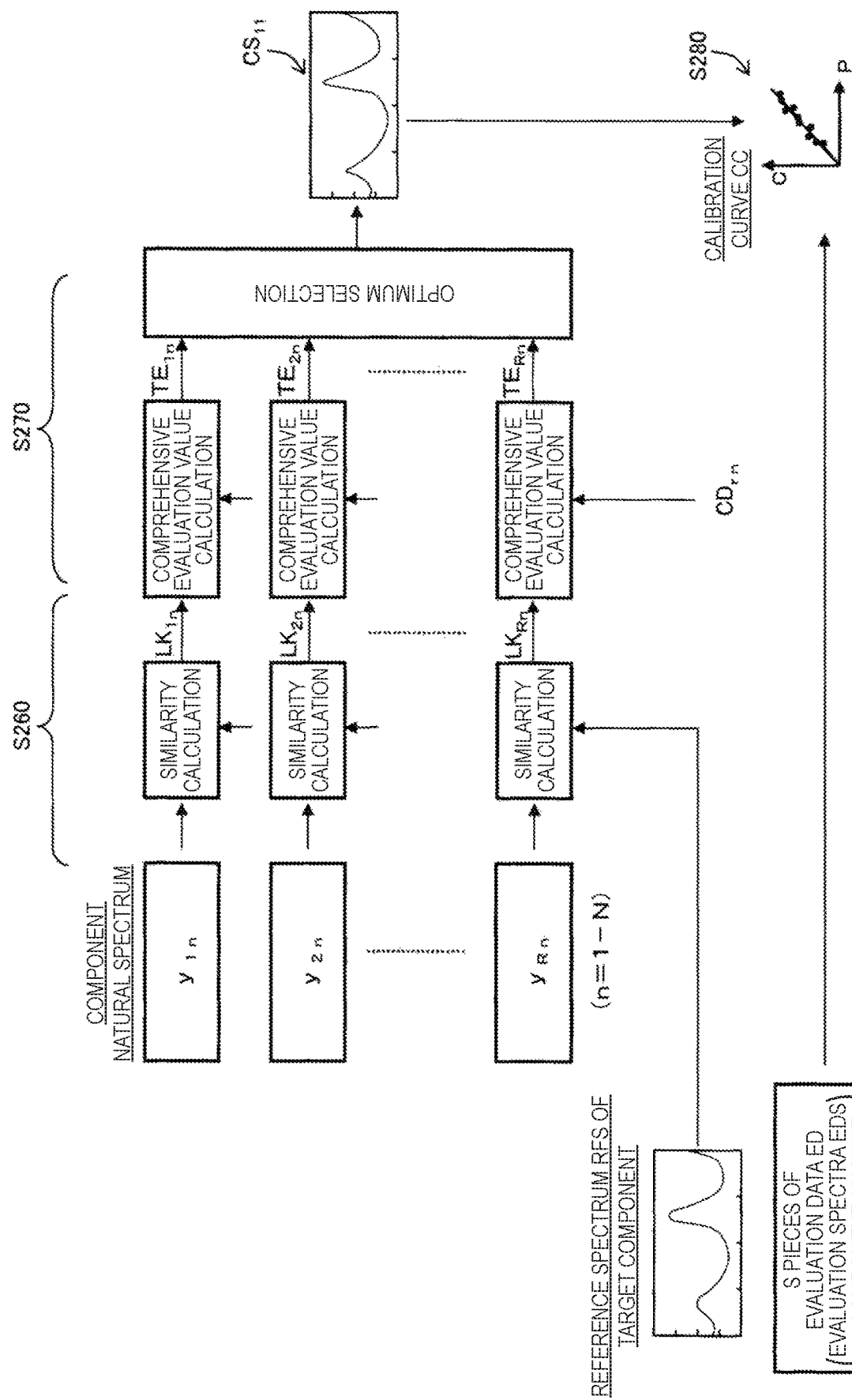
FIG. 8 is a diagram illustrating the content of the calibration data acquisition process.

FIGS. 6, 7 and 8 are flowchart illustrating the calibration data acquisition process in the present embodiment and diagrams illustrating the content thereof, and illustrate detailed steps of step S110 in FIG. 5.

In step S210, measurement is performed on Q (where Q is an integer of 3 or more) first samples containing a plurality of components including a target component (for example, glucose) so that a set of Q optical spectra OS (FIG. 7) is acquired, and measurement is performed on S (where S is an integer of 3 or more) second samples in which a component amount for the target component is known so that S pieces of evaluation data ED (FIG. 7) are acquired. A reference spectrum RFS (FIG. 8) regarding the target component is acquired.

The set of the Q optical spectra OS is learning sample data for determining a component calibration spectrum by performing independent component analysis. The evaluation data ED includes the evaluation spectra EDS which are optical spectra for the S samples and a known component amount for the target component in each sample. In the Q first samples, a component amount for the target component may be known, but samples in which a component amount for the target component is unknown may be used. This is because, in the calibration data acquisition process of the present embodiment, a component amount of the target component in the Q first samples is not used. The number Q of first samples may be any integer of 3 or more, but, if Q is a great value of 100 or more, an effect achieved by the process in FIG. 6 is large. This is because, if the number Q of first samples increases, a component amount distribution is similar to a Gaussian distribution, thus it is difficult to perform independent component analysis in which a component amount is treated as an independent component with high accuracy, and, as a result, it is notably meaningful to create a subset which will be described later. The reason will be supplementarily described below.

In order to perform the above-described independent component analysis in which a component amount is treated as an independent component with high accuracy, a plurality of pieces of sample data (optical spectra) are required, and a set of the sample data preferably satisfies the following conditions.

Condition C1

A plurality of optical spectra are data obtained by performing measurement on a sample in which various components which can be present during actual measurement on a test object except for a specific target component are mixed with each other.

Condition C2

A component amount distribution of a plurality of components including a target component are statistically independent from each other according to a non-Gaussian distribution.

The above condition C1 may be satisfied by performing measurement under various measurement conditions. However, the condition C2 is not ensured to be satisfied in a set of sample data which is prepared at random. Particularly, with respect to data collected from a plurality of different samples, a component amount distribution may be similar to a normal distribution (Gaussian distribution). On the other hand, not with respect to the whole set of samples but with respect to a subset thereof, it is expected that a component amount distribution deviated from a normal distribution can be obtained. Therefore, in the present embodiment, in step S220 which will be described later, a subset is extracted from a set of optical spectra OS of all prepared samples, and thus independent component analysis in which a component amount is treated as an independent component is improved.

The number S of second samples in which a component amount is known may be any integer of 3 or more, and a larger number S is preferable in that calibration accuracy is improved. Typically, the number S of second samples is smaller than the number Q of first samples. Some or all of the second samples may be used as parts of the first samples.

The reference spectrum RFS of the target component is a spectrum which may be regarded to be derived from a target component (for example, glucose), and corresponds to the component natural spectrum $y_n$ described in FIGS. 1 and 2. The reference spectrum RFS is used to select a target component calibration spectrum among a plurality of component calibration spectra obtained through independent component analysis which will be described later. The reference spectrum RFS may be acquired according to various methods, and may be acquired according to, for example, the following method.

Reference Spectrum Acquisition Method 1

A plurality of third samples (for example, aqueous solutions) are created in which concentrations of components other than a target component are constant, and a concentration of the target component is changed to a plurality of values, spectrometry is performed on the plurality of third samples so that a plurality of optical spectra are acquired, and principal component analysis (PCA) is performed on the plurality of optical spectra so that the reference spectrum RFS of the target component is acquired. In the method 1, since a plurality of samples in which only a component concentration for a target component is changed are used, the reference spectrum RFS which can be regarded to be derived from the target component can be obtained by performing the principal component analysis. Some or all of the S (where S is an integer of 3 or more) second samples for acquiring the evaluation data ED may be used as some or all of the plurality of third spectra for acquiring the reference spectrum RFS.

Reference Spectrum Acquisition Method 2

A plurality of human phantoms (simulation human bodies) are created in which a component amount (concentration) for a target component (for example, glucose) is changed, spectrometry is performed on the plurality of human phantoms so that optical spectra are acquired, and changes in the optical spectra are acquired as the reference spectrum RFS of the target component.

Reference Spectrum Acquisition Method 3

A plurality of pieces of artificial blood are created in which a component amount (concentration) for a target component (for example, glucose) is changed, spectrometry is performed on the plurality of pieces of artificial blood so that optical spectra are acquired, and changes in the optical spectra are acquired as the reference spectrum RFS of the target component.

Reference Spectrum Acquisition Method 4

An aqueous solution (for example, a glucose aqueous solution) of a target component is created, subject takes in the aqueous solution, spectrometry is performed on the subject before and after taking in the aqueous solution so that optical spectra are acquired, and a difference between the optical spectra is acquired as the reference spectrum RFS of the target component.

The reason why the reference spectrum RFS of the target component is not used as a target component calibration spectrum without being changed is that a target component calibration spectrum may change depending on a composition of a test object which is a target component calibration object. Specifically, for example, there is a high probability that a glucose calibration spectrum suitable for calibration of a glucose concentration with an aqueous solution containing glucose as a test object, and a glucose calibration spectrum suitable for calibration of a glucose concentration in blood with a human as a test object may have different waveforms. Therefore, in an embodiment described below, independent component analysis is performed on optical spectra obtained through spectrometry on a plurality of first samples having the same composition as that of a test object which is a calibration object, and a spectrum in which a component natural spectrum corresponding to each component calibration spectrum and the reference spectrum RFS have the highest similarity is selected as a target component calibration spectrum from among a plurality of component calibration spectra obtained through the independent component analysis. In the above-described way, the most suitable spectrum corresponding to a target component can be selected as a target component calibration spectrum from among a plurality of component calibration spectra. The content of this process will be further described later.

In step S220, R (where R is an integer of 2 or more) subsets $PA_1$ to $PA_R$ (FIG. 7) are extracted from the set of the Q optical spectra OS. Each of the R subsets $PA_1$ to $PA_R$ is extracted to include M (where M is an integer of 2 or more and below Q) optical spectra OS. The number M of optical spectra OS forming each subset $PA_r$ (where r is 1 to R) is set to a value which is equal to or more than the number of component calibration spectra obtained through the independent component analysis performed in step S230. The numbers M of optical spectra OS forming the respective subsets $PA_r$ (where r is 1 to R) may be values which are different from or the same as each other. Extraction of the subsets $PA_1$ to $PA_R$ is preferably performed at random by using random numbers. In extraction of each subset $PA_r$ (where r is 1 to R), sampling without replacement is used so that the same optical spectrum is not extracted twice or more in the same subset $PA_r$. The number of combinations of selecting M different optical spectra from among the Q optical spectra OS is the same as $_QC_M$. The number R of subsets $PA_r$ may be set to be equal to or less than the number $_QC_M$ of combinations, or may be set to any integer of 2 or more. As mentioned above, if the R subsets $PA_1$ to $PA_R$ are extracted from the Q optical spectra OS prepared in step S210, one or more subsets $PA_r$ satisfying the above condition C2 are expected to be generated.

In step S230, the above-described independent component analysis in which a component amount is treated as an independent component is performed on each of the R subsets $PA_1$ to $PA_R$ so that N (where N is an integer of 1 or more) component natural spectra $y_{r1}$ to $y_{rN}$ with respect to each subset $PA_r$ (where r is 1 to R), and the corresponding N component calibration spectra $CS_{r1}$ to $CS_{rN}$ are obtained (FIG. 7). As a result, a total of R×N component natural spectra $y_{rn}$ and R×N component calibration spectra $CS_{rn}$ (where r is 1 to R, and n is 1 to N) can be acquired. The number N of components is not required to match the number of actually contained components, and is empirically or experimentally determined so that the accuracy of independent component analysis is improved. A value of N may be set to an integer of 1 or more, but may be an integer of 2 or more.

Steps S240 to S270 are processes of selecting an optimal target component calibration spectrum corresponding to the target component from among the R×N component calibration spectra $CS_{rn}$ (where r is 1 to R, and n is 1 to N) obtained in step S230. First, in step S240, an inner product is performed between each of the R×N component calibration spectra $CS_{rn}$ and the S evaluation spectra EDS so that S inner product values P are obtained. In other words, the S inner product values P are calculated for a single component calibration spectrum $CS_{rn}$.

In step S250, a correlation degree $CD_{rn}$ between the known component amount C for the target component in the S second samples and the S inner product values P calculated for the component calibration spectra $CS_{rn}$ are obtained with respect to each of the R×N component calibration spectra $CS_{rn}$. Graphs in which a relationship between the inner product value P and the component amount C of the target component is plotted with respect to each of the component calibration spectra $CS_{rn}$ are drawn on the right end in FIG. 7. As the correlation degree $CD_{rn}$, for example, a correlation coefficient may be used.

In step S260, the similarity $LK_{rn}$ between a corresponding component natural spectra $y_{rn}$ and the reference spectrum RFS of the target component (FIG. 8) is obtained with respect to each of the R×N component calibration spectra $CS_{rn}$.

The similarity $LK_{rn}$ may be calculated according to various methods, and, for example, the following values may be used as the similarity $LK_{rn}$.

(1) A correlation coefficient between the component natural spectrum $y_{rn}$ and the reference spectrum RFS of the target component (2) An inner product between the component natural spectrum $y_{rn}$ and the reference spectrum RFS of the target component (3) An inverse number of norm in a case where a difference between the component natural spectrum $y_{rn}$ and the reference spectrum RFS of the target component is treated as multi-dimensional vector In order to obtain such a value, the component natural spectrum $y_{rn}$ and the reference spectrum RFS of the target component are preferably normalized in advance.

The reference spectrum RFS of the target component may be one, but may be plural. In a case where a plurality of reference spectra RFS are used, first, an individual similarity between each reference spectrum RFS and the component natural spectrum $y_{rn}$ may be calculated, and a comprehensive similarity obtained by combining the individual similarities with each other may be used as the similarity $LK_{rn}$ of the component calibration spectrum $CS_{rn}$ corresponding to the component natural spectrum $y_{rn}$. The comprehensive similarity may be calculated according to various methods, and, for example, a value obtained by multiplying a plurality of individual similarities together or by adding a plurality of individual similarities together may be used as the comprehensive similarity.

In step S270, a comprehensive evaluation value $TE_{rn}$ is calculated by using the correlation degree $CD_{rn}$ calculated in step S250 and the similarity $LK_{rn}$ calculated in step S260 with respect to each of the R×N component calibration spectra $CS_{rn}$. The comprehensive evaluation value may be calculated according to various methods, and, for example, the following values may be used as comprehensive evaluation value $TE_{rn}$.

(1) A value obtained by multiplying the correlation degree $CD_{rn}$ and the similarity $LK_{rn}$ (2) A sum of the correlation degree $CD_{rn}$ and the similarity $LK_{rn}$ (3) An addition value with a weight of the correlation degree $CD_{rn}$ and the similarity $LK_{rn}$ Typically, a function may be set in advance so that the comprehensive evaluation value $TE_{rn}$ is defined by using the function having, as variables, the correlation degree $CD_{rn}$ and the similarity $LK_{rn}$. The function is preferably a function in which, in a case where one of two variables such as the correlation degree $CD_{rn}$ and the similarity $LK_{rn}$ is constant, and the other variable changes, the greater comprehensive evaluation value $TE_{rn}$ is obtained as a value of the changing variable becomes greater.

In step S270, from among the R×N component calibration spectra $CS_{rn}$, a single component calibration spectrum $CS_{rn}$ causing the comprehensive evaluation value $TE_{rn}$ to be greatest (best) is selected as a target component calibration spectrum corresponding to the target component. For example, in a case where the comprehensive evaluation value $TE_{rn}$ regarding the component calibration spectrum $CS_{11}$ is greatest, the component calibration spectrum $CS_{11}$ is selected as a target component calibration spectrum.

In step S280, the single regression formula C=uP+v (refer to FIG. 2) indicating a relationship between the S inner product values P obtained through an inner product between the S evaluation spectra EDS and the target component calibration spectrum $CS_{11}$, and the known component amount C for the target component in the S second samples is created as the calibration curve CC by using the target component calibration spectrum $CS_{11}$ selected in the above-described way. The S inner product values P regarding the target component calibration spectrum $CS_{11}$ are already obtained in step S240, and thus the S inner product values P may be used without being changed in step S280.

As mentioned above, in the present embodiment, since independent component analysis in which component amounts for N components in each sample are treated as independent components is performed, the independent component analysis can be performed with high accuracy, and thus calibration of a target component can be performed with high accuracy, even in a case where optical spectra derived from a plurality of components are not independent from each other. In the present embodiment, a plurality of subsets $PA_r$ are extracted from a set of Q optical spectra OS, and independent component analysis in which a component amount is treated as an independent component is performed on each of the subsets $PA_r$. In the above-described way, even in a case where a component amount distribution in the whole set of the Q optical spectra OS is a Gaussian distribution, and thus there is a subset in which independency is deficient, independency is improved since a component amount distribution is a more non-Gaussian distribution in several subsets $PA_r$, and thus it is possible to obtain a target component calibration spectrum with high accuracy. As a result, it is possible to perform calibration with higher accuracy. In the present embodiment, since, from among the R×N component calibration spectra $CS_{rn}$, a component calibration spectrum causing the comprehensive evaluation value $TE_{rn}$ based on the correlation degree $CD_{rn}$ and the similarity $LK_{rn}$ to be greatest is selected as a target component calibration spectrum, it is possible to determine a target component calibration spectrum suitable for calibration of a sample.

E. EXAMPLE

Creation of Sample

In an Example, an aqueous solution which is a mixture of glucose as a target component, albumin as another component, and water was used as a first sample and a second sample. Specifically, the first sample for acquiring the optical spectra OS is an aqueous solution in which the glucose and the albumin are respectively mixed with pure water in concentration ranges of 50 to 400 mg/dL and 4000 to 5000 mg/dL. Here, component amounts (concentrations) of the glucose and the albumin were set to concentrations determined as random values following a normal distribution in which the set range is included in $3\sigma$ with the center of the set range as an average value. In other words, independent component analysis with high accuracy was expected not to be performed on the entire first sample. The number Q of first samples was 5000.

In the same manner as the first sample, the second sample for acquiring the evaluation data ED is also an aqueous solution in which the glucose and the albumin are respectively mixed with pure water in concentration ranges of 50 to 400 mg/dL and 4000 to 5000 mg/dL. However, the second sample is an aqueous solution in which a true value of the glucose concentration is measured and is known through chemical analysis. In the Example, the number S of second samples was 10.

A third sample for acquiring the reference spectrum RFS of the target component (glucose) is an aqueous solution in which the glucose is mixed with pure water in a concentration range of 50 to 400 mg/dL, and the albumin is in a constant concentration (about 4500 mg/dL). However, the third sample is an aqueous solution in which a true value of the glucose concentration is measured and is known through chemical analysis.

Acquisition of Optical Spectra OS or the Like (Step S210 in FIG. 6)

The optical spectra OS were acquired from the first samples according to the procedures in FIGS. 6 and 7, and the evaluation data ED was acquired from the second samples. First, spectrometry including a near-infrared wavelength region of 1100 to 1300 nm was performed on the 5000 first samples so that 5000 measure spectra were acquired, and preprocessing was performed thereon so that the optical spectra OS were acquired. Similarly, the evaluation spectra EDS were acquired for the ten second samples in which the concentration of the glucose which is a target component is known. Principal component analysis (PCA) was performed on optical spectra obtained through spectrometry on a plurality of third samples so that the reference spectrum RFS of the target component was acquired.

Extraction of Subset (Step S220)

Next, 500 different optical spectra OS were selected from a set of the 5000 optical spectra OS at random, and 10000 subsets $PA_r$ were created. In other words, the number R of subsets $PA_r$ was set to 10000, and the number M of optical spectra OS forming each subset $PA_r$ was set to 500. Here, the number of combinations of selecting 500 from 5000 is $_{5000}C_{500}=1.52\times10^{704}$, and the 10000 subsets $PA_r$ are extremely small parts thereof.

Independent Component Analysis on Subsets (Step S230)

Next, independent component analysis in which a component amount is treated as an independent component was performed on the 10000 subsets $PA_r$ so that three component natural spectra $y_{rn}$ and three component calibration spectra $CS_{rn}$ (where r is 1 to 10000, and n is 1 to 3) corresponding to the three components were obtained. In other words, 30000 component natural spectra $y_{rn}$ and 30000 component calibration spectra $CS_{rn}$ were obtained as a whole.

Calculation of Inner Product Value (Step S240)

Inner products with the 10 evaluation spectra EDS were calculated with respect to each of the component calibration spectra $CS_{rn}$ so that ten inner product values P were obtained.

Calculation of Correlation Degree (Step S250)

The correlation degree $CD_{rn}$ (correlation coefficient) between the inner product value P and the component amount C was computed on the basis of the ten inner product values P regarding each of the component calibration spectra $CS_{rn}$ and the known component amount C (glucose concentration) of the glucose of the second samples.

Calculation of Similarity (Step S260)

The similarity $LK_{rn}$ between a corresponding component natural spectra $y_{rn}$ and the reference spectrum RFS of the target component was calculate with respect to each of the component calibration spectra $CS_{rn}$, and ten similarities $LK_{rn}$ were obtained. As the similarity $LK_{rn}$, a correlation coefficient between the component natural spectra $y_{rn}$ and the reference spectrum RFS of the target component was used.

Calculation of Comprehensive Evaluation Value and Selection of Target Component Calibration Spectrum (Step S270)

The comprehensive evaluation value $TE_{rn}$ was calculated by using the correlation degree $CD_{rn}$ calculated in step S250 and the similarity $LK_{rn}$ calculated in step S260 with respect to each of the component calibration spectra $CS_{rn}$, and the component calibration spectrum $CS_{rn}$ for which the comprehensive evaluation value $TE_{rn}$ was greatest was selected as an optimal target component calibration spectrum corresponding to the glucose (target component). As the comprehensive evaluation value $TE_{rn}$, a value $(CD_{rn}\times LK_{rn})$ obtained by multiplying the correlation degree $CD_{rn}$ and the similarity $LK_{rn}$ was used.

Creation of Calibration Data (Step S280)

The single regression formula C=uP+v indicating a relationship between the ten inner product values P obtained through the inner product between the ten evaluation spectra EDS and the target component calibration spectrum, and the known component amount C for the target component in the ten second samples is created as a calibration curve by using the selected target component calibration spectrum.

In a comparative example, the process (extraction of subsets) in step S220 in FIG. 6 is not performed, independent component analysis in which a component amount was treated as an independent component was performed on the whole set of 5000 optical spectra OS in step S230, and three component natural spectra y and three component calibration spectra CS were determined. The processes in step S240 and the subsequent steps were performed in the same manners as in the above-described Example.

Figure 9:
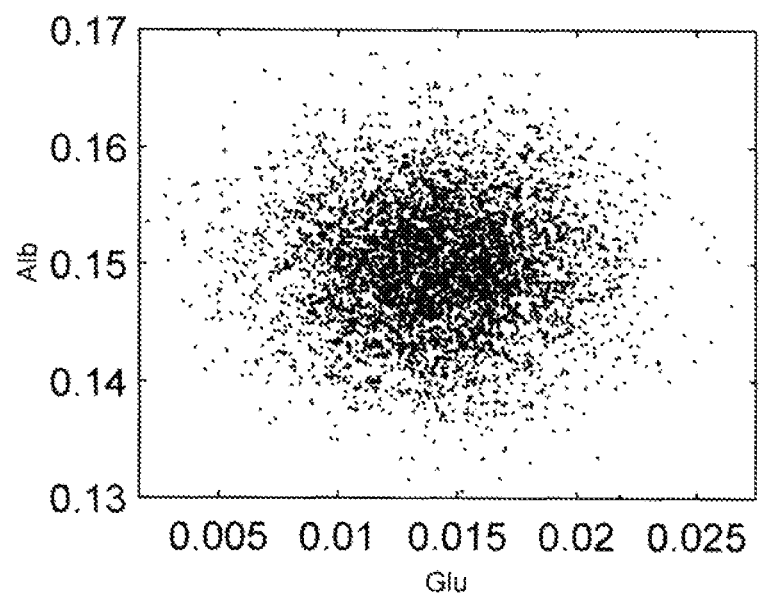
FIG. 9 is a graph illustrating a concentration distribution of components in all samples.
Figure 10:
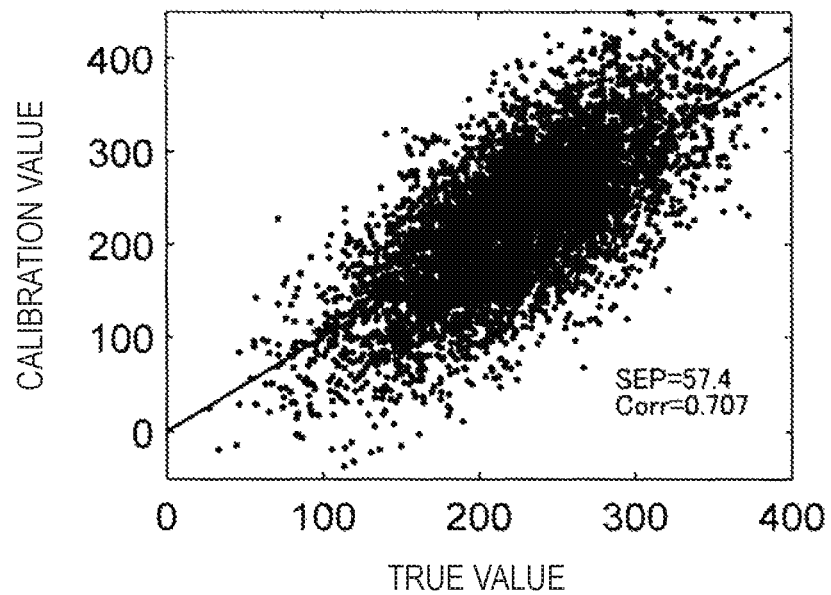
FIG. 10 is a graph illustrating calibration accuracy in a comparative example using all samples.

FIG. 9 is a graph illustrating concentration distributions of glucose and albumin for the 5000 first sample. FIG. 10 is a graph illustrating calibration accuracy in the comparative example, in which a transverse axis expresses a true value of a glucose concentration, and a longitudinal axis expresses a calibration value. In the comparative example, calibration accuracy SEP of the glucose concentration was 57.4 mg/dL, and a correlation coefficient Corr between the calibration value and the true value of the glucose concentration was 0.707. As can be understood from FIG. 10, distributions of the calibration value and the true value are greatly spread, and thus the calibration accuracy is low.

Figure 11:
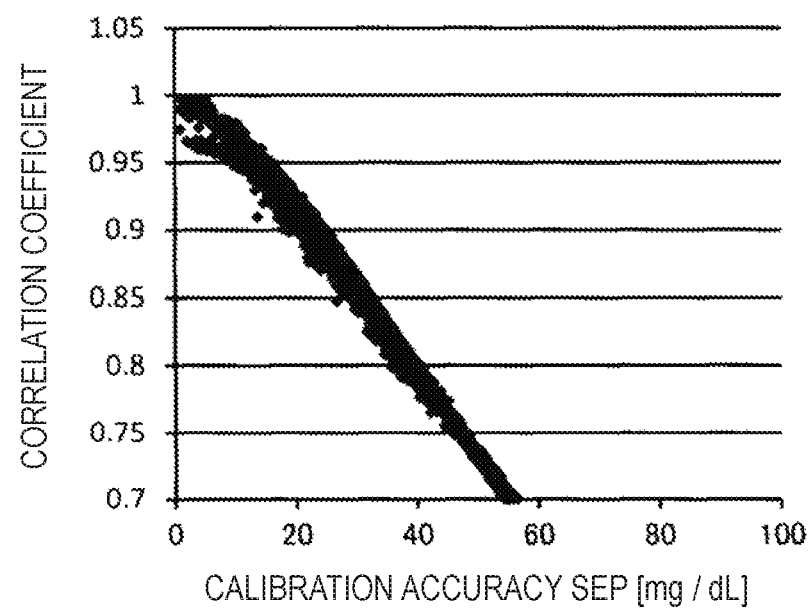
FIG. 11 is a graph illustrating a relationship between calibration accuracy and a correlation coefficient in an Example.

FIG. 11 is a graph illustrating a relationship between the calibration accuracy obtained for the 30000 component calibration spectra $CS_{rn}$ obtained in the Example and a correlation coefficient between the calibration value and the true value. According to this result, it can be seen that, as a correlation coefficient between the calibration value and the true value becomes larger, the calibration accuracy becomes more favorable, and a stronger correlation for both sides is present.

Figure 12:
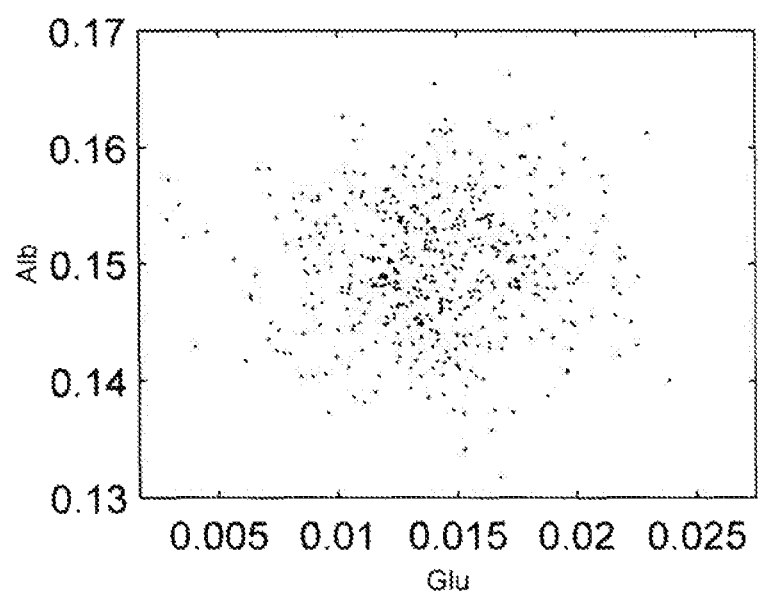
FIG. 12 is a graph illustrating a concentration distribution of components in an optimal subset in the Example.
Figure 13:
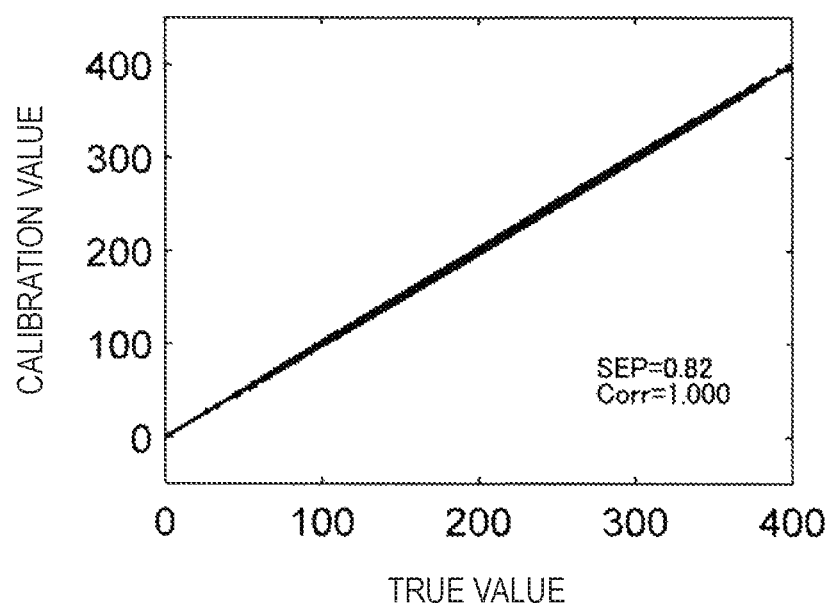
FIG. 13 is a graph illustrating calibration accuracy obtained with an optimal subset in the Example.

FIG. 12 is a graph illustrating concentration distributions of the glucose and the albumin with respect to 500 samples corresponding to the optimal subsets $PA_r$ in the Example. FIG. 13 is a graph illustrating calibration accuracy obtained with the optimal subsets $PA_r$ in the Example. In the Example, the calibration accuracy SEP of the glucose concentration was 0.82 mg/dL, the correlation Corr between the calibration value and the true value of the glucose concentration was 1.000, and both of the two results were more favorable than in the comparative example. Therefore, it was confirmed that the independent component analysis could be performed with high accuracy, and calibration of glucose as a target component could also be performed with high accuracy, according to the methods of the embodiment.

F. MODIFICATION EXAMPLES

The invention is not limited to the above-described embodiment or alternations thereof, and can be implemented in various aspects within the scope without departing from the spirit of the invention and may be modified as follows, for example.

Modification Example 1

In the above-described embodiment and Example, a description has been made of a case where an aqueous solution containing glucose is used as a sample, but the invention is applicable to other samples. For example, the invention is applicable to a case where a liquid containing a salt or liquid containing a protein such as a lipid or albumin or an alcohol is used as a sample. The invention is also applicable to independent component analysis in which other objects such as a human body (human), a voice, and an image are used as samples. In a case where a human body is an object, the invention is applicable with neutral fat or alcohol in the human body, or glucose in blood as a target component. In a case where data or a signal other than a spectrum is an independent component analysis object, the word "spectrum" may be replaced with other words such as "measured data" or "object data".

Modification Example 2

Regarding apparatuses to which the invention is applicable, the invention is also applicable to an apparatus in which a component concentration is estimated on the basis of spectrometric data of an optically mid-infrared spectroscopic type, near-infrared spectroscopic type, or Raman spectroscopic type. The invention is also applicable to any one of an optical protein concentration meter, an optical neutral fat concentration meter, an optical blood glucose meter, an optical salt concentration meter, and an optical alcohol concentration meter.

The entire disclosure of Japanese Patent Application No. 2016-186723 filed Sep. 26, 2016 is hereby incorporated herein by reference.

What is claimed is:

1. A method comprising:
acquiring an optical spectrum obtained through a first spectrometry measurement using a measurement device on a test object;
acquiring, by a computer program being implemented on a computer or a hardware circuit, calibration data including a target component calibration spectrum corresponding to a target component, and a single regression formula indicating a calibration curve;
computing, by the computer program being implemented on the computer or the hardware circuit, an inner product value between the optical spectrum acquired for the test object and the target component calibration spectrum;
calculating, by the computer program being implemented on the computer or the hardware circuit, a component amount for the target component in the test object corresponding to the obtained inner product value by using the single regression formula; and
causing, by the computer program being implemented on the computer or the hardware circuit, a display to display the component amount for the target component in the test object,
wherein in the acquiring of the calibration data,
(a) acquiring, by the computer program being implemented on the computer or the hardware circuit, Q optical spectra obtained through a second spectrometry measurement using the measurement device on Q (where Q is an integer of 3 or more) first samples each containing N (where N is an integer of 1 or more) components including the target component, S evaluation spectra obtained through a third spectrometry measurement using the measurement device on S (where S is an integer of 3 or more) second samples in which a component amount for the target component is known, and a reference spectrum corresponding to the target component obtained using the measurement device,
(b) extracting, by the computer program being implemented on the computer or the hardware circuit, R (where R is an integer of 2 or more) subsets from a set of the Q optical spectra, each of the R subsets containing a corresponding subset of the optical spectra out of the Q optical spectra, a number of the optical spectra of the corresponding subset in the respective R subsets being equal to 2 and less than Q,
(c-1) first determining, by the computer program being implemented on the computer or the hardware circuit, a component natural spectrum matrix formed of N component natural spectra derived from the N components by performing independent component analysis in which component amounts for the N components are treated as independent components in each sample on each of the R subsets,
(c-2) second determining, by the computer program being implemented on the computer or the hardware circuit, N component calibration spectra which are a row vector of a general inverse matrix of the component natural spectrum matrix by performing independent component analysis in which component amounts for the N components are treated as independent components in each sample on each of the R subsets,
(c-3) acquiring, by the computer program being implemented on the computer or the hardware circuit, a total of R×N component natural spectra and R×N component calibration spectra based on the (c-1) first determining and the (c-2) second determining,
(d) obtaining, by the computer program being implemented on the computer or the hardware circuit, S inner product values by performing an inner product between each of the R×N component calibration spectra and the S evaluation spectra,
(e) obtaining, by the computer program being implemented on the computer or the hardware circuit, a correlation degree between a component amount for the target component in the S second samples and the S inner product values with respect to each of the R×N component calibration spectra, (f) obtaining, by the computer program being implemented on the computer or the hardware circuit, a similarity between a component natural spectrum corresponding to each component calibration spectrum and the reference spectrum with respect to each of the R×N component calibration spectra, (g) obtaining, by the computer program being implemented on the computer or the hardware circuit, a comprehensive evaluation value calculated by using the correlation degree and the similarity with respect to each of the R×N component calibration spectra, and, from among the R×N component calibration spectra, selecting, by the computer program being implemented on the computer or the hardware circuit, a component calibration spectrum causing the comprehensive evaluation value to be greatest as the target component calibration spectrum, and (h) creating, by the computer program being implemented on the computer or the hardware circuit, as the calibration curve, the single regression formula indicating a relationship between the inner product values obtained through an inner product between the S evaluation spectra and the target component calibration spectrum, and component amounts for the target component contained in the S second samples.

2. The method according to claim 1,
wherein, in the acquiring of the calibration data, in the (c-1) first determining the (c-2) second determining, and the (c-3) acquiring,
(1) using an equation X=YW in which an optical spectrum matrix X having optical spectra obtained through a spectrometry measurement using the measurement device on each sample as column vectors is the same as a product between a component natural spectrum matrix Y having unknown component natural spectra derived from the N respective components contained in each sample as column vectors and a component amount matrix W having unknown component amounts for the N components in each of the samples as column vectors, and performs independent component analysis in which the respective column vectors forming the component amount matrix W are treated as independent components, so as to determine the component amount matrix W and the component natural spectrum matrix Y, and
(2) employing inverse matrix row vectors respectively corresponding to the N components in a general inverse matrix $Y^{\dagger}$ of the component natural spectrum matrix Y determined through the independent component analysis, as the component calibration spectra corresponding to the respective components.

3. A calibration curve creation method of creating a calibration curve used to obtain a component amount for a target component contained in a test object, the method comprising:

(a) acquiring, by a computer program being implemented on a computer or a hardware circuit, Q optical spectra obtained through a first spectrometry measurement using a measurement device on Q (where Q is an integer of 3 or more) first samples each containing N (where N is an integer of 1 or more) components including the target component, S evaluation spectra obtained through a second spectrometry measurement using the measurement device on S (where S is an integer of 3 or more) second samples in which a component amount for the target component is known, and a reference spectrum corresponding to the target component obtained using the measurement device;

(b) extracting, by the computer program being implemented on the computer or the hardware circuit, R (where R is an integer of 2 or more) subsets from a set of the Q optical spectra, each of the R subsets containing a corresponding subset of the optical spectra out of the Q optical spectra, a number of the optical spectra of the corresponding subset in the respective R subsets being equal to 2 and less than Q;

(c-1) first determining, by the computer program being implemented on the computer or the hardware circuit, a component natural spectrum matrix formed of N component natural spectra derived from the N components by performing independent component analysis in which component amounts for the N components are treated as independent components in each sample on each of the R subsets;

(c-2) second determining, by the computer program being implemented on the computer or the hardware circuit, N component calibration spectra which are a row vector of a general inverse matrix of the component natural spectrum matrix by performing independent component analysis in which component amounts for the N components are treated as independent components in each sample on each of the R subsets;

(c-3) acquiring, by the computer program being implemented on the computer or the hardware circuit, a total of R×N component calibration spectra based on the (c-1) first determining and the (c-2) second determining;

(d) obtaining, by the computer program being implemented on the computer or the hardware circuit, S inner product values by performing an inner product between each of the R×N component calibration spectra and the S evaluation spectra;

(e) obtaining, by the computer program being implemented on the computer or the hardware circuit, a correlation degree between a component amount for the target component in the S second samples and the S inner product values with respect to each of the R×N component calibration spectra;

(f) obtaining, by the computer program being implemented on the computer or the hardware circuit, a similarity between a component natural spectrum corresponding to each component calibration spectrum and the reference spectrum with respect to each of the R×N component calibration spectra;

(g) obtaining, by the computer program being implemented on the computer or the hardware circuit, a comprehensive evaluation value calculated by using the correlation degree and the similarity with respect to each of the R×N component calibration spectra, and, from among the R×N component calibration spectra, selecting, by the computer program being implemented on the computer or the hardware circuit, a component calibration spectrum causing the comprehensive evaluation value to be greatest as the target component calibration spectrum; and (h) creating, by the computer program being implemented on the computer or the hardware circuit, as the calibration curve, the single regression formula indicating a relationship between the inner product values obtained through an inner product between the S evaluation spectra and the target component calibration spectrum, and the component amounts for the target component contained in the S second samples.

* * * * *